United States Patent
Sitek et al.

(10) Patent No.: US 11,302,044 B2
(45) Date of Patent: Apr. 12, 2022

(54) METHOD OF DETERMINING CONTRAST PHASE OF A COMPUTERIZED TOMOGRAPHY IMAGE

(71) Applicant: International Business Machines Corporation, Armonk, NY (US)

(72) Inventors: Arkadiusz Sitek, Ashland, MA (US); Benedikt Graf, Charlestown, MA (US); Yiting Xie, Cambridge, MA (US); Amin Katouzian, Lexington, MA (US); Yusuke Takeuchi, Boston, MA (US); Paul Dufort, Toronto (CA)

(73) Assignee: International Business Machines Corporation, Armonk, NY (US)

( * ) Notice: Subject to any disclaimer, the term of this patent is extended or adjusted under 35 U.S.C. 154(b) by 157 days.

(21) Appl. No.: 16/926,880

(22) Filed: Jul. 13, 2020

(65) Prior Publication Data

US 2022/0012927 A1    Jan. 13, 2022

(51) Int. Cl.

| | |
|---|---|
| G06T 11/00 | (2006.01) |
| G06N 20/00 | (2019.01) |
| G06N 5/04 | (2006.01) |
| G06T 7/00 | (2017.01) |
| G06K 9/62 | (2022.01) |
| A61B 6/03 | (2006.01) |

(Continued)

(52) U.S. Cl.
CPC .......... *G06T 11/008* (2013.01); *A61B 5/7267* (2013.01); *A61B 6/032* (2013.01); *A61B 6/504* (2013.01); *A61B 6/5217* (2013.01); *G06K 9/6267* (2013.01); *G06N 5/04* (2013.01); *G06N 20/00* (2019.01); *G06T 7/0012* (2013.01);

(Continued)

(58) Field of Classification Search
CPC ....... A61B 5/7267; A61B 6/032; A61B 6/504; A61B 6/5217; G06K 9/6267; G06N 20/00; G06N 5/04; G06T 11/008; G06T 2207/10081; G06T 2207/20081; G06T 2207/20084; G06T 2207/30056; G06T 2207/30096; G06T 7/0012
See application file for complete search history.

(56) References Cited

U.S. PATENT DOCUMENTS

| | | | |
|---|---|---|---|
| 2011/0002520 A1* | 1/2011 | Suehling | G06T 7/0012 382/131 |
| 2012/0070055 A1 | 3/2012 | Liu et al. | |
| 2014/0016846 A1 | 1/2014 | Blaskovics et al. | |

OTHER PUBLICATIONS

Philbrick et al., "What Does Deep Learning See? Insights From a Classifier Trained to Predict Contrast Enhancement Phase From CT Images." American Journal of Roentgenology, 211: 6, 2018, 10 pages.

(Continued)

*Primary Examiner* — Manuchehr Rahmjoo
(74) *Attorney, Agent, or Firm* — Jeffrey M. Ingalls

(57) ABSTRACT

A computer-implemented method for classifying and presenting a contrast phase (CP) of a contrast enhanced computerized tomography (CECT) scan is provided. The method includes training an artificial intelligence (AI) algorithm utilizing a set of CPs labeled CECT data to associate a set of characteristics of the data with a probability associated with the CP. The method includes receiving a new set of unlabeled CECT data, and applying the AI algorithm to the new unlabeled CECT data to associate a first probability of a first CP and a second probability of a second CP. The method also includes providing a graphical representation including the first probability of the first CP and the second probability of the second CP.

20 Claims, 9 Drawing Sheets

(51) Int. Cl.
*A61B 6/00* (2006.01)
*A61B 5/00* (2006.01)
*G06T 9/00* (2006.01)

(52) U.S. Cl.
CPC ............... *G06T 2207/10081* (2013.01); *G06T 2207/20081* (2013.01); *G06T 2207/20084* (2013.01); *G06T 2207/30056* (2013.01); *G06T 2207/30096* (2013.01)

(56) References Cited

OTHER PUBLICATIONS

Tang et al., "Contrast Phase Classification with a Generative Adversarial Network." (Submitted on Nov. 14, 2019), https://arxiv.org/abs/1911.06395, 8 pages.

Philbrick et al., "RIL-Contour: a Medical Imaging Dataset Annotation Tool for and with Deep Learning." Journal of Digital Imaging. 32(4), Aug. 2019, 11 pages.

Sofka et al., "Automatic contrast phase estimation in CT volumes." Med Image Comput Comput Assist Interv. 14 (Pt 3), 2011, 9 pages, Springer-Verlag Berlin Heidelberg 2011.

Dercle et al., "Using a single abdominal Computed Tomography image to differentiate five contrast-enhancement phases: a machine-learning algorithm for radiomics-based precision medicine." European J. Radiology, in press, journal pre-proof; Online: Jan. 28, 2020, 108850. https://doi.org/10.1016/j.ejrad.2020.108850, 32 pages.

Zhou et al., "CT Data Curation for Liver Patients: Phase Recognition in Dynamic Contrast-Enhanced CT." (Submitted on Sep. 5, 2019 (this version), latest version Sep. 27, 2019 (v2)), https://arxiv.org/abs/1909.02511v1, 11 pages.

Mell et al., "The NIST Definition of Cloud Computing", Recommendations of the National Institute of Standards and Technology, Special Publication 800-145, Sep. 2011, 7 pages.

\* cited by examiner

METHOD OF DETERMINING CONTRAST PHASE OF A COMPUTERIZED TOMOGRAPHY IMAGE

BACKGROUND

The present disclosure relates to computer-implemented methods, systems and computer program products to determine a contrast phase of a contrast-enhanced (CE) computed (or computerized) tomography (CT) image. Artificial intelligence (AI) and deep learning systems may be used to train anomaly detection models related to a CT volume, and then the model is used with new CT volume data to attempt to identify visual anomalies (e.g., a tumor) in the contrast-enhanced computed tomography (CECT) images. The contrast medium used in the CECT scans has different contrast phases (CPs) that occur during different time periods after administration. Certain visual anomalies may appear differently in certain of the different contrast phases. Knowledge or identification of the contrast phase may be helpful to generate more accurate anomaly detection results.

SUMMARY

Embodiments of the present disclosure relate to a computer-implemented method for classifying and presenting a contrast phase (CP) of a contrast enhanced computerized tomography (CECT) scan is provided. The method includes training an artificial intelligence (AI) algorithm utilizing a set of CPs labeled CECT data to associate a set of characteristics of the data with a probability associated with the CP. The method includes receiving a new set of unlabeled CECT data, and applying the AI algorithm to the new unlabeled CECT data to associate a first probability of a first CP and a second probability of a second CP. The method also includes providing a graphical representation including the first probability of the first CP and the second probability of the second CP.

Other embodiments of the present disclosure are directed to a computer system and computer program product for performing the method.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, explain the principles of the disclosure. The drawings are only illustrative of certain embodiments and do not limit the disclosure.

Figure 1:
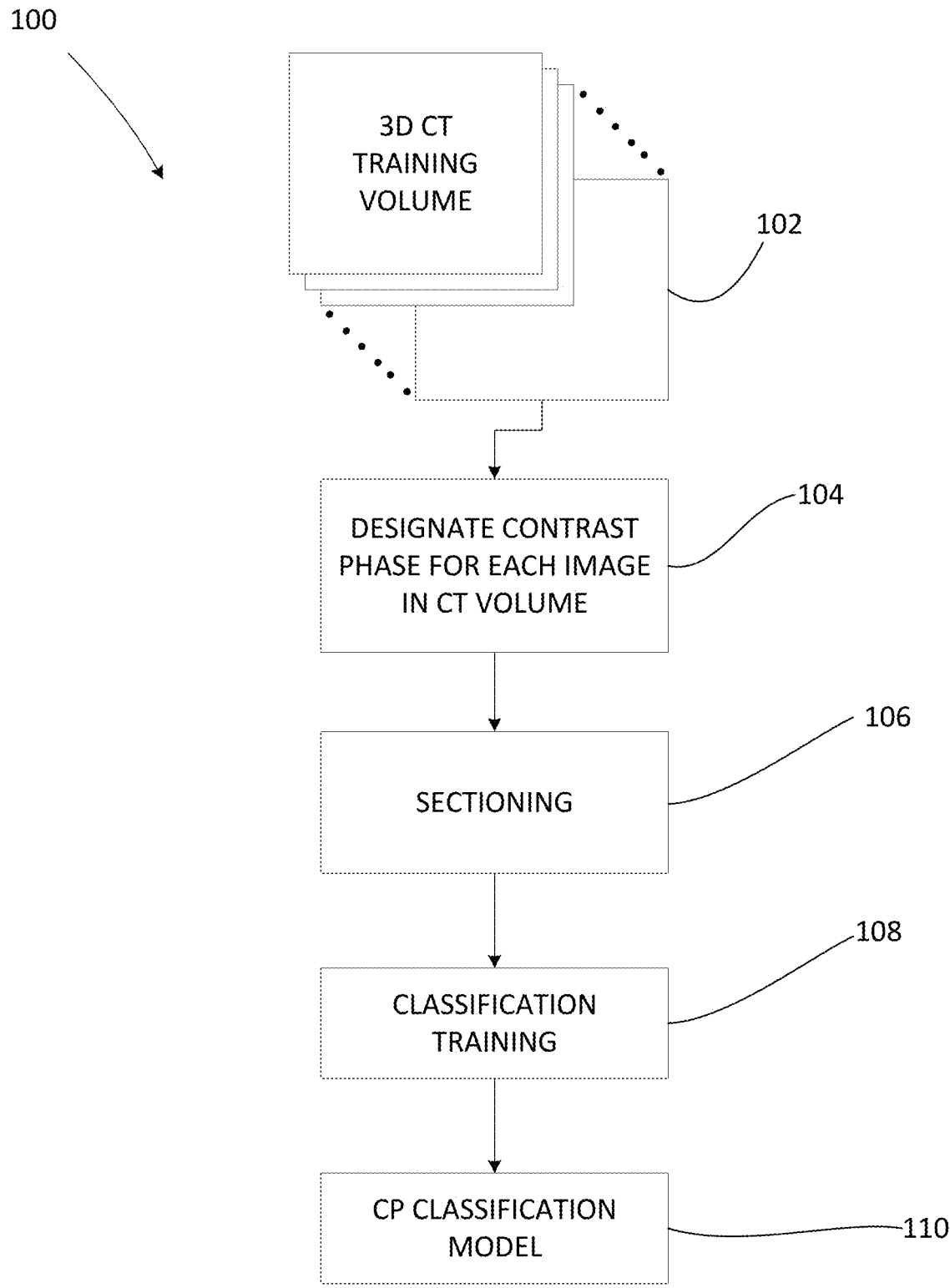
FIG. 1 is a flow chart illustrating an example of utilizing AI and/or a recurrent neural network to train a contrast phase (CP) classification model, according to embodiments.

It should be appreciated that elements in the figures are illustrated for simplicity and clarity. Well-understood elements that may be useful or necessary in a commercially feasible embodiment may not be shown for the sake of simplicity and to aid in the understanding of the illustrated embodiments.

DETAILED DESCRIPTION

The present disclosure relates to methods, systems and computer program products to identify a contrast phase of a contrast-enhanced (CE) computed (or computerized) tomography (CT) image. In certain embodiments, artificial intelligence (AI) and deep learning systems are utilized to identify probabilities that a CECT image is in a given contrast phase. In certain embodiments, the determined probabilities are presented to a user in a graphical representation.

In general, a CT scan is a medical imaging procedure that uses computer-processed combinations of many X-ray measurements taken from different angles to produce cross-sectional images of specific areas of a scanned object. In certain applications, contrast agents are used during the CT examinations to highlight specific tissues and parts of the body. Bones can generally be clearly seen on x-ray images without utilizing a contrast agent because of the density difference between the bone and the surrounding tissue. Having sufficient image contrast can aid in perceiving a difference in the density between different areas of a CT image. However, the visualization of certain other organs and soft tissues can be more difficult. Insufficient image contrast can make the identification of a disease or condition more challenging due to the difficulty in differentiating pathological tissues (for example tumors, metastases and abscesses) from normal organ structures and surrounding tissues.

Contrast agents may be used in in contrast-enhanced computed tomography (CECT) studies of various body parts to achieve opacification of a tissue of interest (e.g., kidney CT or liver CT) in relation to the background tissue. Abdominal CECT is the current standard in the assessment of various biological abnormalities (e.g., lesions in a liver).

In liver applications, there are different types of lesions which, in general, can be classified as malignant (e.g., hepatocellular carcinoma, cholangiocarcinoma, angiosarcoma, metastasis, and other malignant lesion) or benign (e.g., hemangioma, focal nodular hyperplasia, adenoma, cyst or lipoma, and granuloma). A main purpose of CECT liver scans is to be able to differentiate between different type of lesions, as this analysis may be helpful to guide subsequent interventions. The CECT liver scan may also be used to analyze healthy liver parenchyma at different phases/stages of the lifecycle of the contrast, and then compare these results to actual liver lesions at these different contrast phases. Based on these differences, classification of the lesion may be performed.

In order to accurately classify the type of lesion seen in a CECT liver scan, a multi-phase study may be conducted. In general, certain types of tissues (e.g., a tumor) appear different based on the amount of time that has elapsed after the contrast has been administered to the patient. Other factors (e.g., a metabolic rate or heart rate of a patient) can affect how long each phase of the contrast may last. In certain types of liver CECT studies, an example protocol includes four phases (time periods) of the contrast. A first phase of the contrast may be referred to as the pre-contrast phase (PRE) where contrast has not yet been administered. Therefore, in this first PRE phase, the images correspond to a normal volumetric CT scan (i.e., without the use of a CE agent). A second phase of the contrast may be referred to as the arterial phase (ART). In this second phase, images are acquired soon after administration of the bolus while the contrast is distributed within the liver through the hepatic arteries of the liver. In this second phase, early enhancement of the lesion may be seen if the lesion has arterial circulation. A third phase of the contrast may be referred to as the portal venous phase (VEN), and this phase corresponds to a state when the contrast reaches hepatic portal circulation and is being drained from the liver through the hepatic veins. The portal circulation is a major source of blood supply during this third phase of the contrast. A fourth phase of the contrast may be referred to as the delayed scan phase (DEL), and during this phase a retention of contrast material in, for example, lesions and parenchyma may be seen. It should be appreciated that the present embodiments apply to CECT scans having any suitable number of CPs. For example, other CPs may include early-arterial and nephrogenic CPs.

Although the example of the application of CECT scans to a liver has been discussed, it should be appreciated that other medical imaging applications are applicable to the present embodiments. For example, CECT may be used to detect a pulmonary embolism. In this case, data is acquired while first-pass contrast (FP) has not cleared the lung. This is done to visualize the blockage of blood supply due to a blood clot or another cause. Other applications of CECT scans may be used to analyze other organs or biological abnormalities. In general, the present embodiments may be applied to any situation where contrast is injected into a patient and then distributed throughout the body using the blood supply. As discussed above, during the distribution of the contrast, certain phases can be identified (e.g., PRE, ART, VEN and DEL for the example of the liver CECT).

In the present embodiments, neural networks, artificial intelligence (AI), and other deep learning systems may be utilized to aid in automated determination of a contrast phase during a CECT scan. In general, AI can be applied to medical imaging applications, and includes the application of certain algorithms to certain medical images (e.g., CT volumes) to identify certain visual features. However, as discussed above, when utilizing CECT, different types of tissues can appear with different levels of image contrast depending on the phase of the contrast. Thus, an AI model developed for a PRE phase of the contrast may not work well when analyzing images in the ART, VEN or DEL phases of the contrast. That is, multiple AI models may be needed to accurately and consistently identify abnormalities for different phases of the contrast. For example, the contrast may need to be in the lung vasculature to detect pulmonary edema.

The information regarding what contrast phase is present for a given medical image may or may not be in the Digital Imaging and Communications in Medicine (DICOM) metadata that is associated with the CECT volume (or images of the volume). Even if this information is available, it may not be reliable. In related techniques that do not include an AI-based CP classifier model and that do not include DICOM metadata regarding the CP of the CT volume images, it may be necessary for a user (e.g., a physician) to manually enter their subjective determination of the contrast phases.

When developing AI solutions, it may be helpful to know what phase of the contrast the image is in to be able to apply appropriate AI processing (e.g., PRE scan will not work well for classification of liver lesions or detection abnormalities as dissection, etc.). In another example, the VEN phase may not be optimal for detecting PE. The present embodiments provide systems and methods to enable automatic determination of the likelihood that a particular CECT image is in particular contrast phase, and then display these results to a user in an intuitive and easy to comprehend manner.

In the present embodiments, after a CP classification model has been previously trained, a CT volume having an unknown contrast phase status is analyzed by, for example, convolutional neural networks and probability scores are determined for each possible phase based on the CP classification model. The probability indicates a likelihood of which contrast phase a given CECT volume (or given image of a volume) is in.

In general, an Artificial Neural Network (ANN) (also referred to more generally as a neural network) is a computing system made up of a number of simple, highly interconnected processing elements (nodes), which process information by their dynamic state response to external inputs. ANNs are processing devices (algorithms and/or hardware) that are loosely modeled after the neuronal structure of the mammalian cerebral cortex, but on much smaller scales. Such systems progressively and autonomously learn tasks by means of examples, and they have successfully been applied to, for example, speech recognition, text processing and computer vision. A large ANN might have hundreds or thousands of processor units, whereas a mammalian brain has billions of neurons with a corresponding increase in magnitude of their overall interaction and emergent behavior.

Many types of neural networks are known, starting with feedforward neural networks, such as multilayer perceptrons, deep learning neural networks (DNNs) and convolutional neural networks. A feedforward neural network is an artificial neural network (ANN) where connections between the units do not form a cycle. A deep learning neural network is an artificial neural network with multiple hidden layers of units between the input and output layers. Similar to shallow ANNs, DNNs can model complex non-linear relationships. DNN architectures, e.g., for object detection and parsing, generate compositional models where the object is expressed as a layered composition of image primitives. The extra layers enable composition of features from lower layers, giving the potential of modeling complex data with fewer units than a similarly performing shallow network. DNNs are typically designed as feedforward networks.

In certain embodiments described herein, systems, methods and computer program products are provided that use Artificial Intelligence (AI) to facilitate contrast phase image detection with regard to different CECT image sources. Machine learning, which is a subset of AI, utilizes algorithms to learn from data (e.g., Big Data) and create foresights based on this data. AI refers to the intelligence when machines, based on information, are able to make decisions, which maximize the chance of success in a given topic. More specifically, AI is able to learn from a data set to solve problems and provide relevant recommendations. AI is a subset of cognitive computing, which refers to systems that learn at scale, reason with purpose, and naturally interact with humans. Cognitive computing is a mixture of computer science and cognitive science. Cognitive computing utilizes self-teaching algorithms that use data, visual recognition, and natural language processing to solve problems and optimize processes.

Referring now to the drawings in which like numerals represent the same or similar elements and initially to FIG. 1, this figure illustrates an example of a method 100 of utilizing AI and/or a recurrent neural network to train a contrast phase (CP) classification model, according to embodiments. Once trained, the CP classification model can be used on new volumes (or images) to make determinations as to probabilities that the given volume (or image) corresponds to one or more contrast phases. For example, a first image of an object taken during a first contrast phase (e.g., a PRE phase) may have visual differences (e.g., contrast, color, etc.) from a second image of the same object taken during a second contrast phase (e.g., an ART phase). The trained CP classification model uses AI to analyze new images and determine which contrast phase the image is likely in. Thus, in certain embodiments, for new CT volumes, user input may not be required to determine which CP the image is in. It should be noted that, in certain embodiments, the application of the CP classification is for determination of which contrast phase the image is in, and it is not used to identify the visual anomalies that may be present in the image. Once the image is classified as being in a particular CP, another AI model can then be selected and used to actually identify the anomalies. In this regard, multiple AI anomaly detection models may be trained, with each of the different AI anomaly detection models corresponding to a different one of the contrast phases. One AI anomaly detection model may not be suitable for a particular CP where the contrast for a particular visual anomaly are low, but it may work very well with a different CP where the contrast characteristics for the particular visual anomaly are high.

The visualization of the probabilities obtained by the model may present certain challenges. First, the CP boundaries between phases may be difficult to define. Therefore, there may be scans that occur at a point in time between two or more different CP states. One way to unify the description of CP may be to specify an amount of time that has elapsed after the injection of contrast. However, this method may suffer from a problem that depending on the metabolism of the subject (e.g., the patient), the actual CP may vary substantially between subjects considered at the same amount of time that has elapsed after injection of the contrast. Second, CP status may be cyclical. Therefore, for very late scans, CT volumes may either resemble a late scan or a pre-contrast injection scan. Therefore, relying solely on the amount of elapsed time after injection may create a serious discontinuity in the scores (i.e., one of the images could resemble either time zero or time 600 seconds (i.e., a late scan)). According to certain of the present embodiments, the outcome of the model is represented as probabilities that the volume is in a certain CP, and these probabilities are visualized using a cyclical visualization technique.

As shown in FIG. 1, at operation 102, a three-dimensional CT training volume is provided that will be used to train the CP classification model. In certain embodiments, the CT training volume includes a plurality of different images of an object (e.g., a liver). In operation 104, each of these images are assigned or designated a contrast phase. Thus, prior to performing the AI classification training of the CP classification model in operation 108, it is assumed that the contrast phase of each of the images is known or has been otherwise determined. In certain embodiments, a doctor (or user) may examine each of the images and manually make determinations as to which of a plurality of different contrast phases the subject image is in. In alternate embodiments, rather than having a user make a manual designation of the CP of each image in the CT volume, AI systems may be used to classify the contrast phase of the particular image. That is, although the embodiments described above herein with respect to FIG. 1 are directed to training a CP classification model, AI systems may be used (i.e., as an alternative to, or in conjunction with user input) to help determine the CPs for the training images. In an example, AI systems may determine Hounsfield unit (HU) values in various parts of the vasculature (e.g., ascending/descending aorta, pulmonary artery, pulmonary vein, portal vein, etc.), and those HU values may be used to determine the contrast phase. In certain embodiments, average Hounsfield units (AHUs) values are used to infer certain contrast injection parameters such as the concentration of contrast, the injection rate of the contrast, the injection duration, etc. Therefore, this AI analysis (or pre-classification) of CP for the images of the CT training volume may aid in facilitating the overall training process of the CP classification model. In other embodiments, the pre-classification of the CP by the AI systems may be provided to a user, and then the user may confirm or override the pre-classification according to their judgment.

As shown in FIG. 1, in operation 106, each CT volume is divided axially in N overlapped sections. Each section is one instance used for training. In operation 108, the CP classified images of the 3D CT training volume are processed by the AI systems to perform training. At operation 110, the CP classification model is created and is ready to use to classify new data (i.e., new CT volumes).

Figure 2:
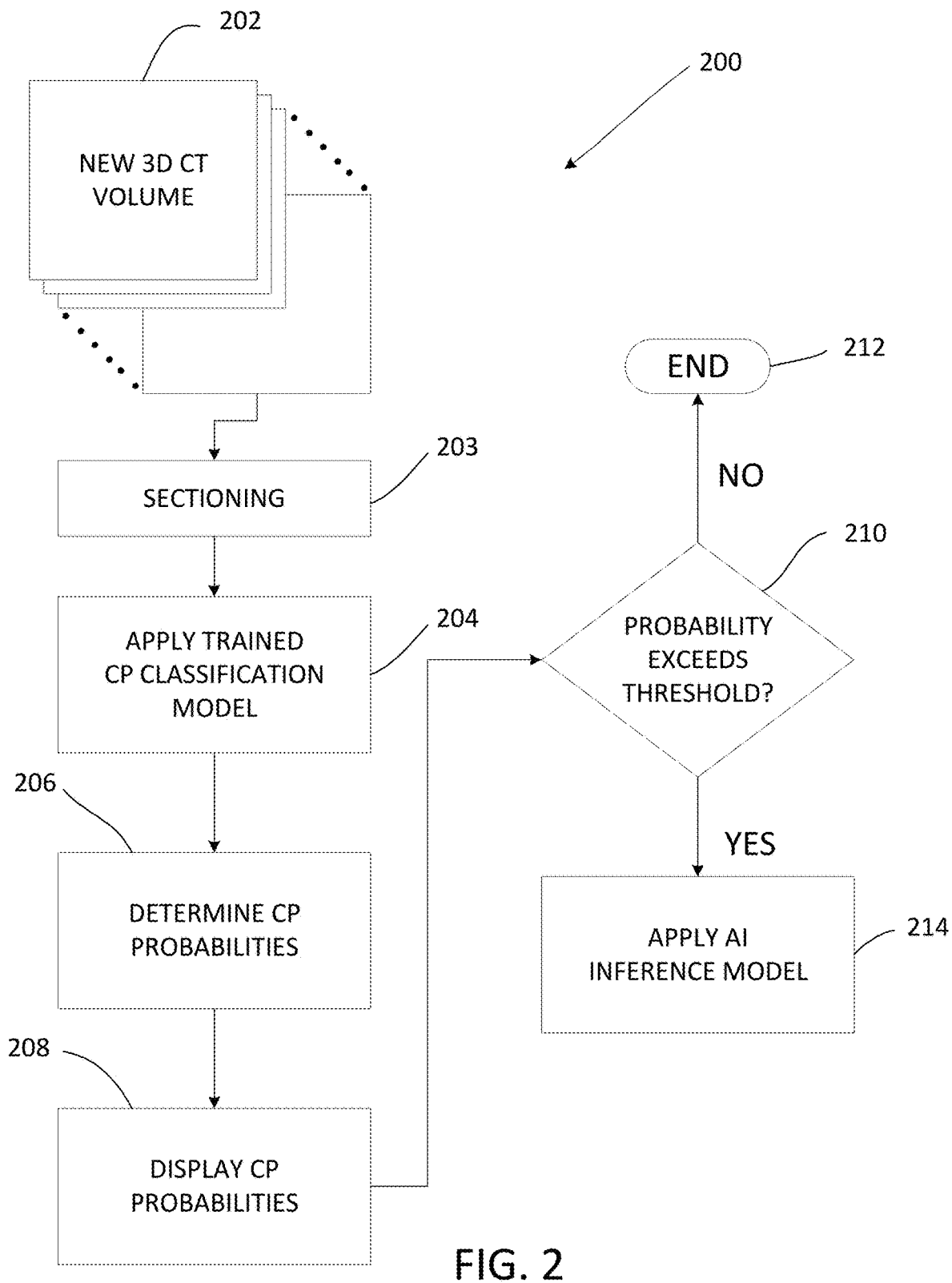
FIG. 2 is a flow chart illustrating an example of the application of the trained CP classification model to a new CT volume to determine the CP, according to embodiments.

Referring now to FIG. 2, this figure illustrates an example method 200 of the application of the trained CP classification model to a new CT volume to determine the CP for each of the new images. In operation 202, a new 3D CT volume is provided. The new CT volume includes a plurality of new images that are different from the images used in training the CP classification model. As shown in FIG. 2, in operation 203, each CT volume is divided axially in N overlapped sections. In operation 204, the trained CP classification model is applied to each of the images in the new CT volume. In operation 206, the AI system determines the probabilities that a given image falls into a certain contrast phase (CP). For example, if there are four contrast phases, the AI system may determine that a first image has a 64% probability of being in a first CP, a 30% probability that the image is in a second CP, a 4% probability that the image is in a third CP, and a 2% probability that the image is in a fourth CP. In certain embodiments, at operation 208, the AI system generates and displays a visual representation of these probabilities on a display device.

At operation 210 in FIG. 2, the AI system determines whether the probability for a given CP for a given image exceeds a certain threshold. For example, a requisite threshold (or probability, or score) may be 60%. Thus, in the example above, the first image of the new CT volume having a 64% probability of being in the first CP exceeds the threshold level of 60%, and therefore is it determined to be in this CP. If it is determined that the image does not meet the requisite threshold (operation 210:NO), then the image is not further processed by the AI system to determine the presence of abnormalities/anomalies. If it is determined that the image does meet the requisite threshold (operation 210:YES), then the AI system applies an AI inference model to determine the presence of abnormalities/anomalies at operation 214. In certain embodiments, a different AI inference model is developed for each of the different contrast phases (e.g., four different AI inference models corresponding to the PRE, ART, VEN and DEL contrast phases). In other embodiments, a single AI inference model is used that considers the contrast phase determined by the AI system at operation 206.

In certain of the present embodiments, the scores obtained from contrast phase classification model are used for further processing by AI systems to determine a suitability of the scan for further processing (e.g., abnormality detection processing). In one example, for analysis of liver lesions, VEN scans may be defined as those scans with a probability of occurring in the VEN contrast phase, where such a probability is larger than a particular threshold level. In other words, the CP classification model may triage new CECT volumes to determine whether or not they are in the CP of interest for a particular type of anomaly. For example, if the CP classification model determines that there is a low likelihood that a particular new CECT is in the VEN phase, it will not be further analyzed to determine the presence of anomalies.

Figure 3A:
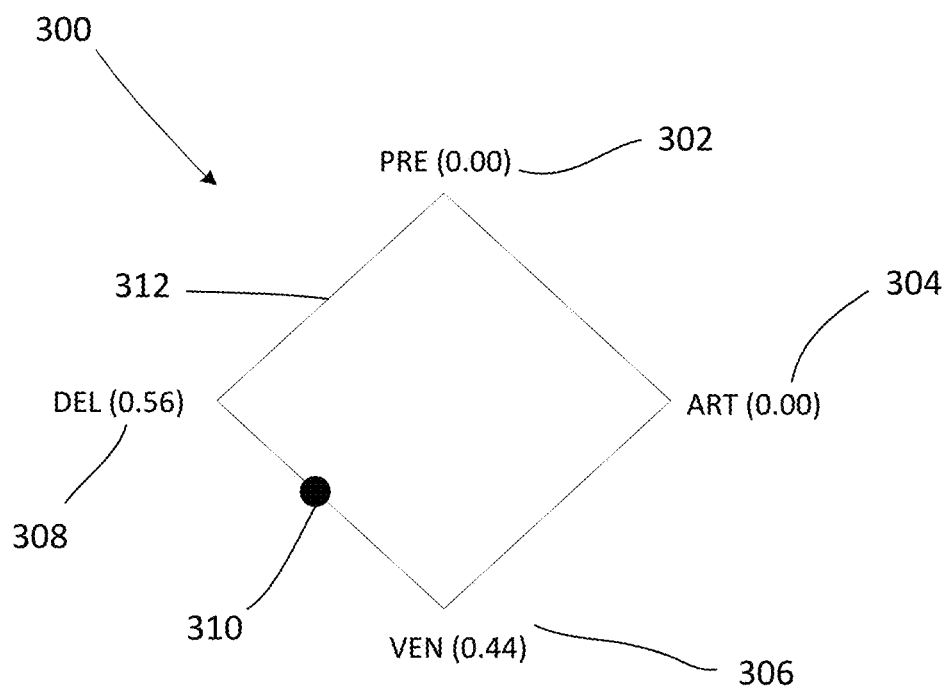
FIG. 3A is a diagram of an example of a visual representation of probabilities of certain CPs as determined by the CP classification model, according to embodiments.

In certain embodiments, probability scores obtained from phase classification are used to generate an intuitive visualization (or graphic representation 300) for a user, so that the user can readily understand the likelihood of a phase of the contrast for a particular CECT image. Referring now to FIG. 3A, an example of a graphic representation is shown. In FIG. 3A, an example of a four-sided polygon 312 (e.g., a diamond or a square) is displayed. In general, the CP probabilities are visualized using regular polygons where each of the corners represents a single CP. In certain embodiments, the actual visualization of the CP for a particular image in the CT volume is represented by a point 310 (or some other suitable shape, marker or indicator) located within the polygon 312 or on the edge of the polygon 312. In the example shown in FIG. 3A, a four-sided polygon 312 is shown that corresponds to four different contrast phases: pre-contrast (PRE); arterial (ART); venous (VEN); and delayed (DEL). Each corner of the polygon 312 corresponds to a pure phase (i.e., a 100% probability that the image is in the particular contrast phase). In the example shown in FIG. 3A, the PRE phase 302 probability is 0%, the ART phase 304 probability is 0%, the VEN phase 306 probability is 44%, and the DEL phase 308 probability is 56%. Thus, the point 310 corresponding to the subject image (e.g., subject image 350 of FIG. 3B) lies exactly on the line between the VEN phase 306 and the DEL phase 308. If there were a greater than 0% probability for one (or both) of the PRE phase 302 and the ART phase 304, then the point 310 would occur within the main area of the polygon 312 somewhat closer to one (or both) of the vertices of the polygon corresponding to the PRE phase 302 and the ART phase 304. Thus, in the example shown in FIG. 3A, there is only a slightly higher percentage chance that the subject image is in the DEL phase 308 than the VEN phase 306.

Figure 3B:
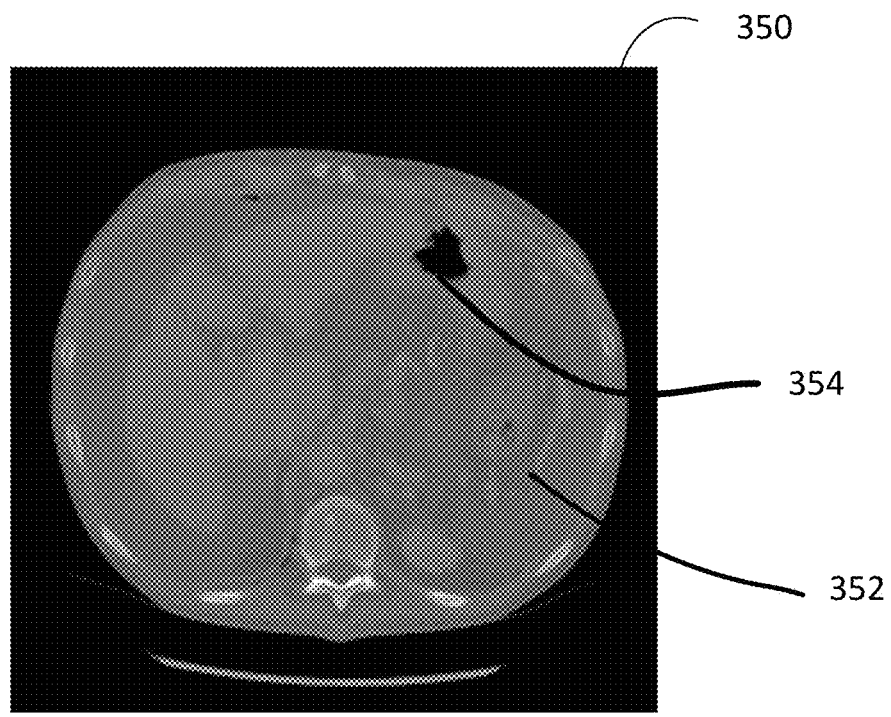
FIG. 3B is an example image from a CT volume illustrating contrast between a visual anomaly and the surrounding tissues, according to embodiments.

Referring now to FIG. 3B, the subject image 350 includes an anomaly 354 and the surrounding tissue 352 of, for example, a liver. As shown in FIG. 3B, there is an amount of contrast between the darker anomaly 354 and the relative lighter surrounding tissue 352. In general, this anomaly 354 appears quite distinct to an observer, and would seem to be readily identifiable. However, assuming that this subject image 350 corresponds to the output of the CP classification model (i.e., the graphic representation 300) discussed above with respect to FIG. 3A, then even though the anomaly appears in stark contrast to the surrounding tissue it may not correlate well with either the a DEL anomaly detection model or a VEN anomaly detection model. In this particular example, the subject image 350 may have been taken at a particular moment in time when the VEN phase 306 was transitioning to the DEL phase 308 (or vice versa). Assuming this image was taken during such a phase transition, there may be visual characteristics of the image that do not apply well to either of the AI-based anomaly detection models. Therefore, this particular image may not be selected for further AI inferencing because the none of the CP probabilities (or scores) generated by the CP classification model exceeded the threshold level, as discussed above with respect to operation 210 of FIG. 2.

In certain embodiments, a decision as to whether a particular volume (or particular image within the volume) is to be processed by AI for anomaly detection may be made based on the determined contrast phase (CP). In certain embodiments, this is done automatically based on the thresholds discussed above. In other embodiments, this may be done manually by a radiologist (or user) using the probability visualizations (or graphical representations) discussed herein. In the embodiments where the user makes a manual determination of the contrast phase based on the visualization, the user looks at the graphical visualization and makes a subjective determination as to what phase they believe the image is most likely to be based on the position of the point 310 in the polygon 312. For example, if the point 310 appears close to one of the vertices of the polygon 312, the user may be confident that it is in a particular CP.

Figure 4A:
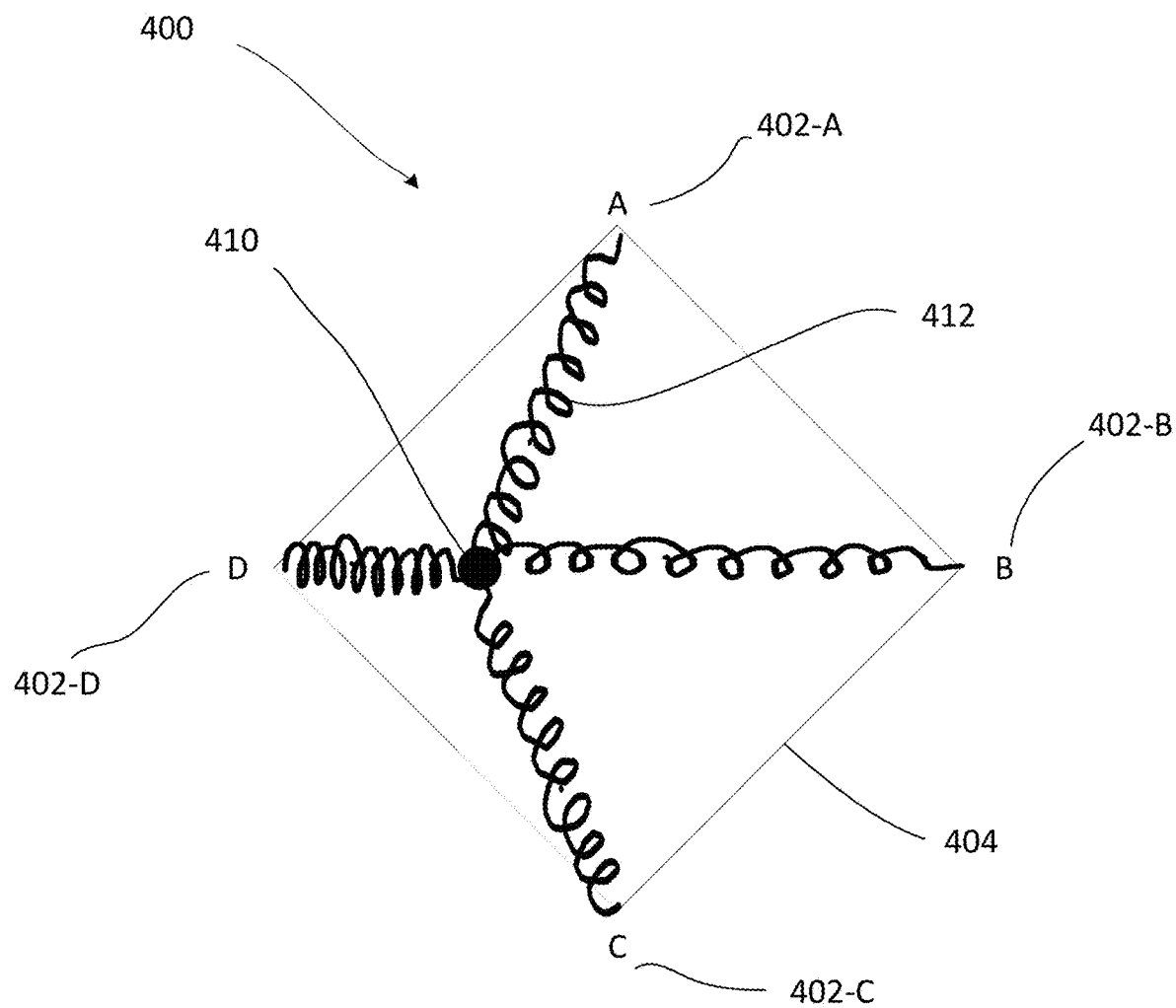
FIG. 4A is a diagram of an example of a visual representation of probabilities of certain CPs for a given image in a CT volume as determined by the CP classification model, according to embodiments.

Referring now to FIG. 4A, this figure shows a diagram of an example of a visual representation of the probabilities of certain CPs for a given image in a CT volume as determined by the CP classification model, according to embodiments. In the example shown in FIG. 4A, a graphical representation 400 including a four-sided polygon 404 is shown that corresponds to four different contrast phases: an A-phase 402-A; a B-phase 402-B; a C-phase 402-C and a D-phase 402-D. Each corner (or vertex) of the polygon 404 corresponds to a pure phase (i.e., a 100% probability that the image is in the particular contrast phase). Similar to the example discussed above with respect to FIG. 3A, a point 410 is shown in the polygon 404 which reflects the relative probabilities that the image falls into a particular contrast phase. The closer the point 410 is to a particular vertex of the polygon, the higher percentage the probability is that the volume (or image) corresponds to the respective CP associated with that vertex. In certain embodiments, the graphical representation 400 also includes one or more additional visual indicators of these probabilities. In this example, the graphical representation 400 includes graphical representation of springs 412. The location of the point 410 is determined based on an equilibrium point assuming it is attached to corners of the display using perfect springs 412 with a stiffness constant equal to the probability that the given volume (or image) is in the given phase determined by the model. The rest length of all springs 412 is assumed to be zero. In this example graphical representation, the probability of the D-phase 402-D is the largest, the spring 412 connecting the point 410 with the D-phase 402-D vertex is the stiffest, and the equilibrium point 410 is closest to the D-phase 402-D vertex.

Figure 4B:
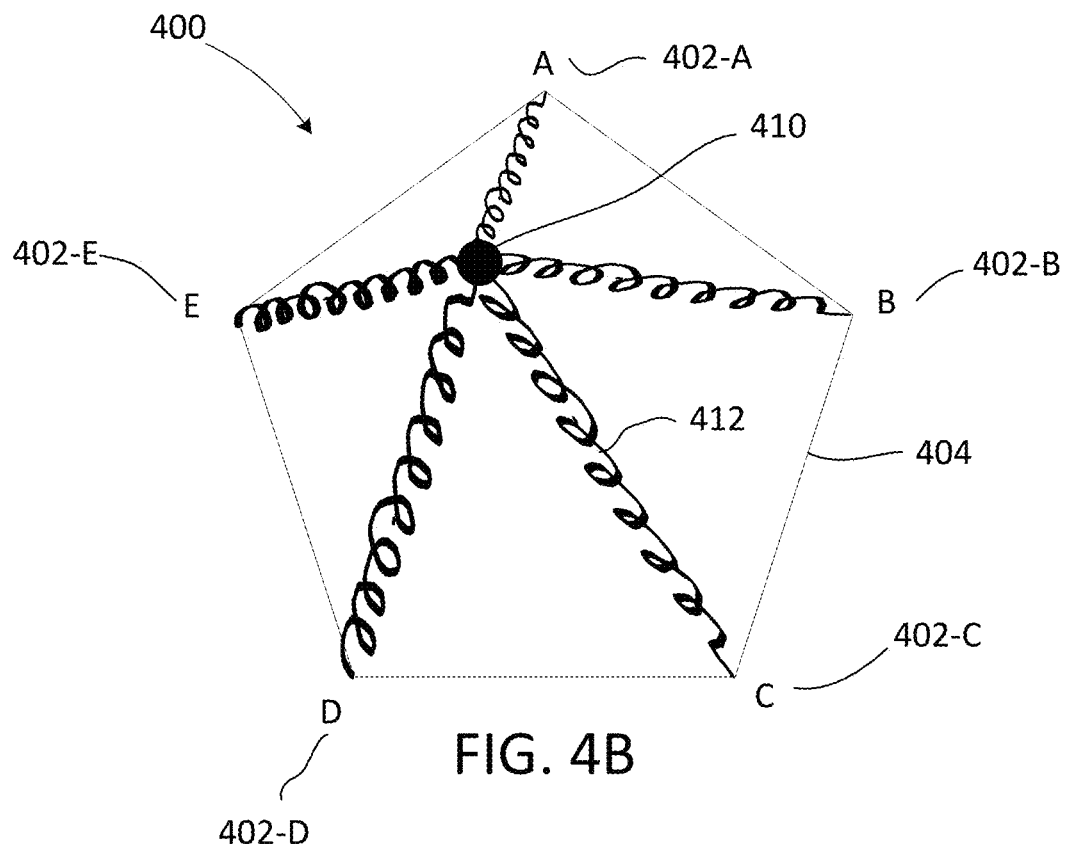
FIG. 4B is a diagram of an example of a visual representation of probabilities of certain CPs for a given image in a CT volume as determined by the CP classification model, according to embodiments.

Referring now to FIG. 4B, this figure shows a diagram of another example of a visual representation of the probabilities of certain CPs for a given image in a CT volume as determined by the CP classification model, according to embodiments. In the example shown in FIG. 4B, a graphical representation 400 including a five-sided polygon 404 is shown that corresponds to five different contrast phases: an A-phase 402-A; a B-phase 402-B; a C-phase 402-C; a D-phase 402-D; and an E-phase 402-E. Similar to FIG. 4A discussed above, the corner (or vertex) of the polygon 404 corresponds to a pure phase (i.e., a 100% probability that the image is in the particular contrast phase). Similar to the example discussed above with respect to FIG. 4A, a point 410 is shown in the polygon 404 which reflects the relative probabilities that the volume (or image) falls into a particular contrast phase. The closer the point 410 is to a particular vertex of the five-sided polygon, the higher percentage the probability is that the image corresponds to the respective CP associated with that vertex. In this example, the graphical representation 400 also includes springs 412. In this example graphical representation, the probability of the A-phase 402-A is the largest, the spring 412 connecting the point 410 with the A-phase 402-A vertex is the stiffest, and the equilibrium point 410 is closest to the A-phase 402-A vertex.

Figure 4C:
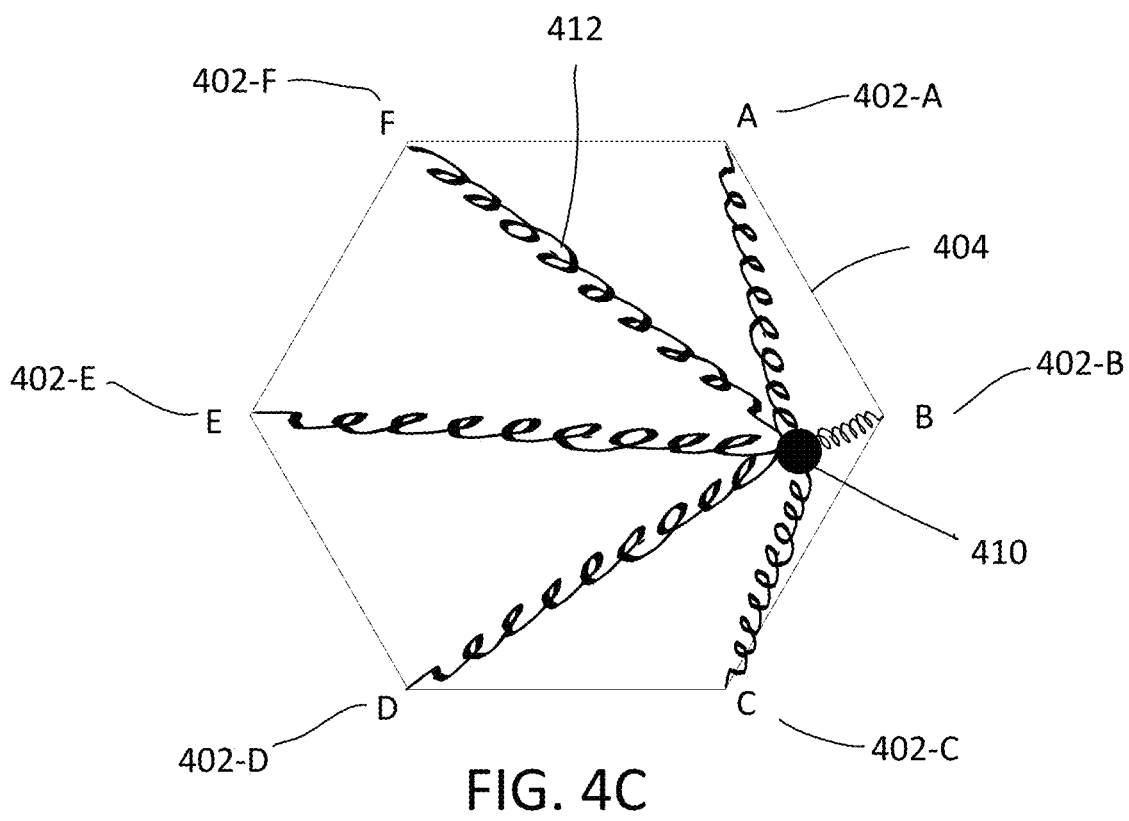
FIG. 4C is a diagram of an example of a visual representation of probabilities of certain CPs for a given image in a CT volume as determined by the CP classification model, according to embodiments.

Referring now to FIG. 4C, this figure shows a diagram of another example of a visual representation of the probabilities of certain CPs for a given image in a CT volume as determined by the CP classification model, according to embodiments. In the example shown in FIG. 4C, a graphical representation 400 including a six-sided polygon 404 is shown that corresponds to six different contrast phases: an A-phase 402-A; a B-phase 402-B; a C-phase 402-C; a D-phase 402-D; an E-phase 402-E; and an F-phase 402-F. Similar to FIG. 4A discussed above, the corner (or vertex) of the polygon 404 corresponds to a pure phase (i.e., a 100% probability that the image is in the particular contrast phase). Similar to the example discussed above with respect to FIG. 4A, a point 410 is shown in the polygon 404 which reflects the relative probabilities that the volume (or image) falls into a particular contrast phase. The closer the point 410 is to a particular vertex of the six-sided polygon, the higher percentage the probability is that the volume (or image) corresponds to the respective CP associated with that vertex. In this example, the graphical representation 400 also includes springs 412. In this example graphical representation, the probability of the B-phase 402-A is the largest, the spring 412 connecting the point 410 with the B-phase 402-B vertex is the stiffest, and the equilibrium point 410 is closest to the B-phase 402-B vertex.

Figure 5:
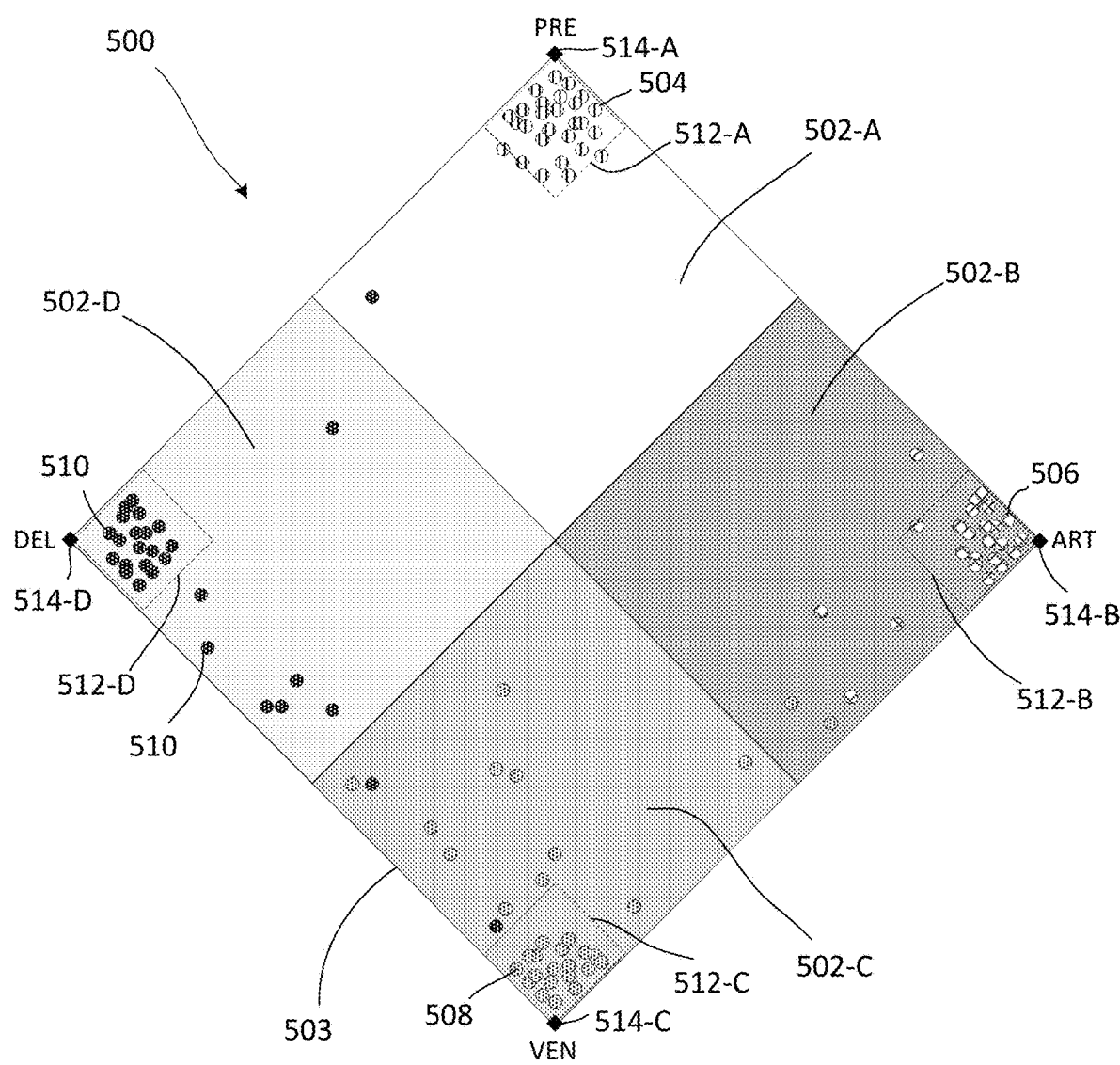
FIG. 5 is a diagram of an example of a visual representation of probabilities of certain CPs for a plurality of images of a CT volume as determined by the CP classification model, according to embodiments.

Referring now to FIG. 5, this figure is a diagram of an example of a visual representation of the probabilities of certain CPs for a plurality of images of a CT volume as determined by the CP classification model, according to embodiments. In the example shown in FIG. 5, a graphical representation 500 including a four-sided polygon 503 is shown that corresponds to four different contrast phases: a PRE phase 514-A; an ART phase 514-B; a VEN phase 514-C and a DEL phase 514-D. Each corner (or vertex 514-A, 514-B, 514-C, 514-D) of the polygon 503 corresponds to a pure phase (i.e., a 100% probability that the image is in the particular contrast phase). A plurality of points 504, 506, 508, 510 are shown located at different positions in the interior of the polygon 503 which reflect the relative probabilities that the image falls into a particular contrast phase. The closer the point 504, 506, 508, 510 is to a particular vertex of the polygon 503, the higher the likelihood is that the volume (or image) corresponds to the respective CP associated with that vertex. In certain embodiments, as shown in FIG. 5, the polygon 503 is divided into sections 502-A, 502-B, 502-C and 502-D corresponding to the different contrast phases.

In operation, as the AI system cycles through each of the images in the CT volume, the CP classification model will generate a point for each of the images. Each image will have an actual contrast phase (the phase that the contrast is actually in), and the AI system attempts to determine what this phase is by applying the CP classification model. In FIG. 5, the points in the polygon 503 have four different types of cross-hatching to signify what the actual contrast phase is. In particular, all of the points 504 with vertical hatching correspond to points that are actually in the PRE phase, all of the points 506 with crisscross hatching correspond to points that are actually in the ART phase, all of the points 508 with light hatching correspond to points that are actually in the VEN phase, and all of the points 510 with dark hatching correspond to points that are actually in the DEL phase. The position of the various points in the polygon 503 reflects the output of the CP classification model for the particular images. For example, a majority of the points 508 are located in a region 512-C close to the vertex 514-C. This proximity indicates that the CP classification model determined a high probability (e.g., 90%) that the image occurs in the VEN CP. However, some of the points 508 appear outside the region 512-C but within the section 502-C that is associated with the VEN CP. For these points, the CP classification model has determined that the image is in the VEN CP, but with a lower probability. Moreover, some of the points 508 may occur in, for example, the section 502-B associated with the ART CP. For these points, the CP classification model has essentially misclassified the images as being in the wrong CP. One possible reason for this is that the CP was transitioning between two different phases where it may be difficult for the CP classification model to determine the correct CP. As described above with respect to operation 210 of FIG. 2, some of these classifications (or misclassifications) may have probability scores that are below a determined threshold. Thus, these images may not be selected for anomaly detection by the AI systems because it is not clear what CP the image is in, and it is difficult to determine which AI anomaly detection model to apply to the image. As mentioned above, one AI anomaly detection model that is developed for a particular CP phase (e.g., the ART phase) may not work well for an image that is in a different CP phase (e.g., the VEN phase). It should be appreciated that the diamond shaped four-sided graphical representation 500 shown in FIG. 5 could be modified for any different number of CPs (e.g., the six-sided polygon shown in FIG. 4C). Therefore, the example graphical representation 500 shown in FIG. 5 provides a reviewer with an easy to understand distribution of where the CP probabilities fall for a plurality of CECT images.

Figure 6:
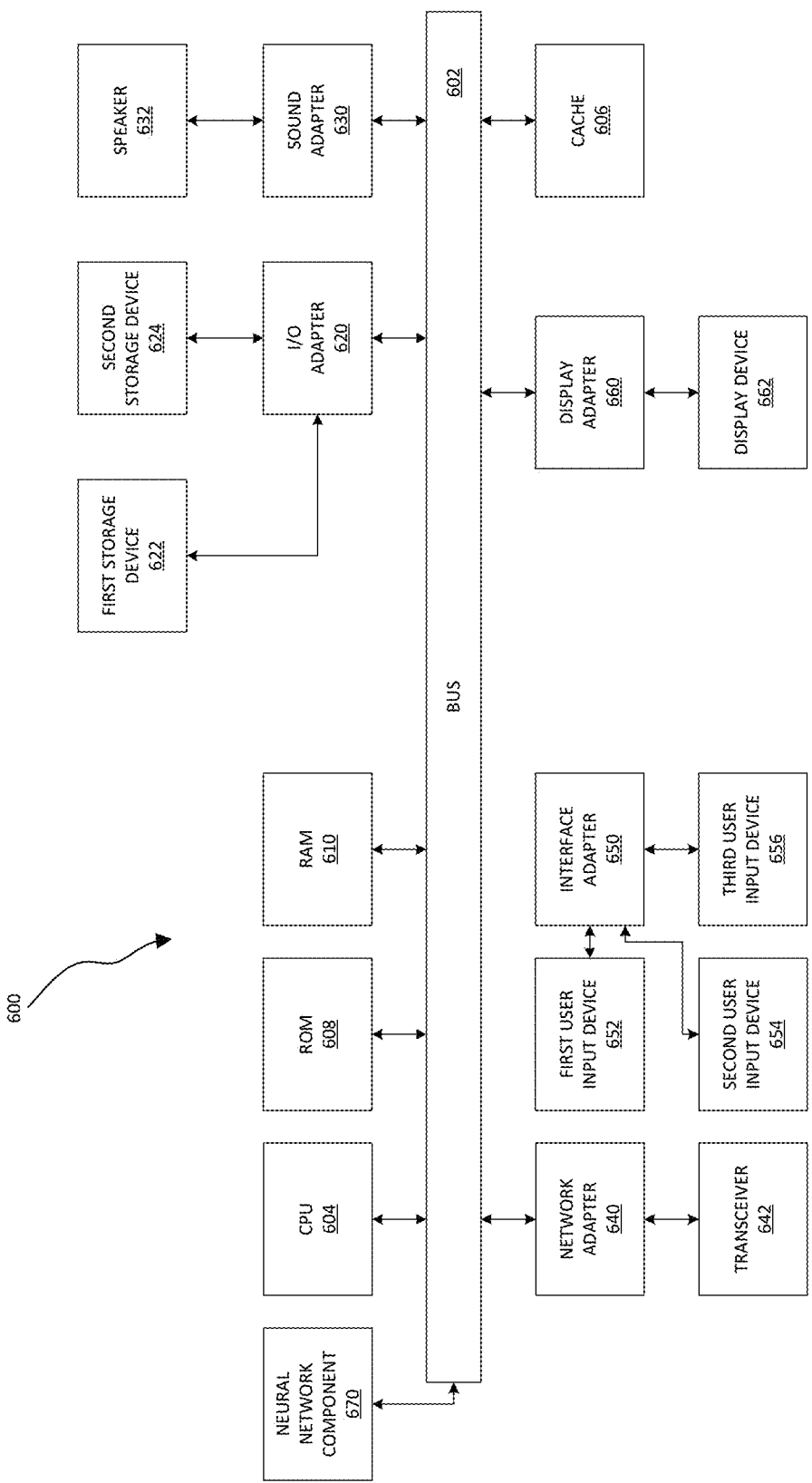
FIG. 6 is a block diagram of a processing system, according to embodiments.

Referring now to FIG. 6, an exemplary processing system 600 to which the present embodiments may be applied is shown in accordance with one embodiment. The processing system 600 includes at least one processor (CPU) 604 operatively coupled to other components via a system bus 602. A cache 606, a Read Only Memory (ROM) 608, a Random-Access Memory (RAM) 610, an input/output (I/O) adapter 620, a sound adapter 630, a network adapter 640, a user interface adapter 650, and a display adapter 660, are operatively coupled to the system bus 602.

A first storage device 622 and a second storage device 624 are operatively coupled to system bus 602 by the I/O adapter 620. The storage devices 622 and 624 may be any of a disk storage device (e.g., a magnetic or optical disk storage device), a solid-state magnetic device, and so forth. The storage devices 622 and 624 may be the same type of storage device or different types of storage devices.

A speaker 632 is operatively coupled to system bus 602 by the sound adapter 630. A transceiver 642 is operatively coupled to system bus 602 by network adapter 640. A display device 662 is operatively coupled to system bus 602 by display adapter 660.

A first user input device 652, a second user input device 654, and a third user input device 656 are operatively coupled to system bus 602 by user interface adapter 650. The user input devices 652, 654, and 656 may be any of a keyboard, a mouse, a keypad, an image capture device, a motion sensing device, a microphone, a device incorporating the functionality of at least two of the preceding devices, or any other suitable types of input devices. The user input devices 652, 654, and 656 may be the same type of user input device or different types of user input devices. The user input devices 652, 654, and 656 are used to input and output information to and from system 600. In certain embodiments, a neural network component 670 with a CP classification mode is operatively coupled to system bus 602.

The processing system 600 may also include other elements (not shown), as readily contemplated by one of skill in the art, as well as omit certain elements. For example, various other input devices and/or output devices may be included in processing system 600, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 600 are readily contemplated by one of ordinary skill in the art given the teachings of the present disclosure provided herein.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 7:
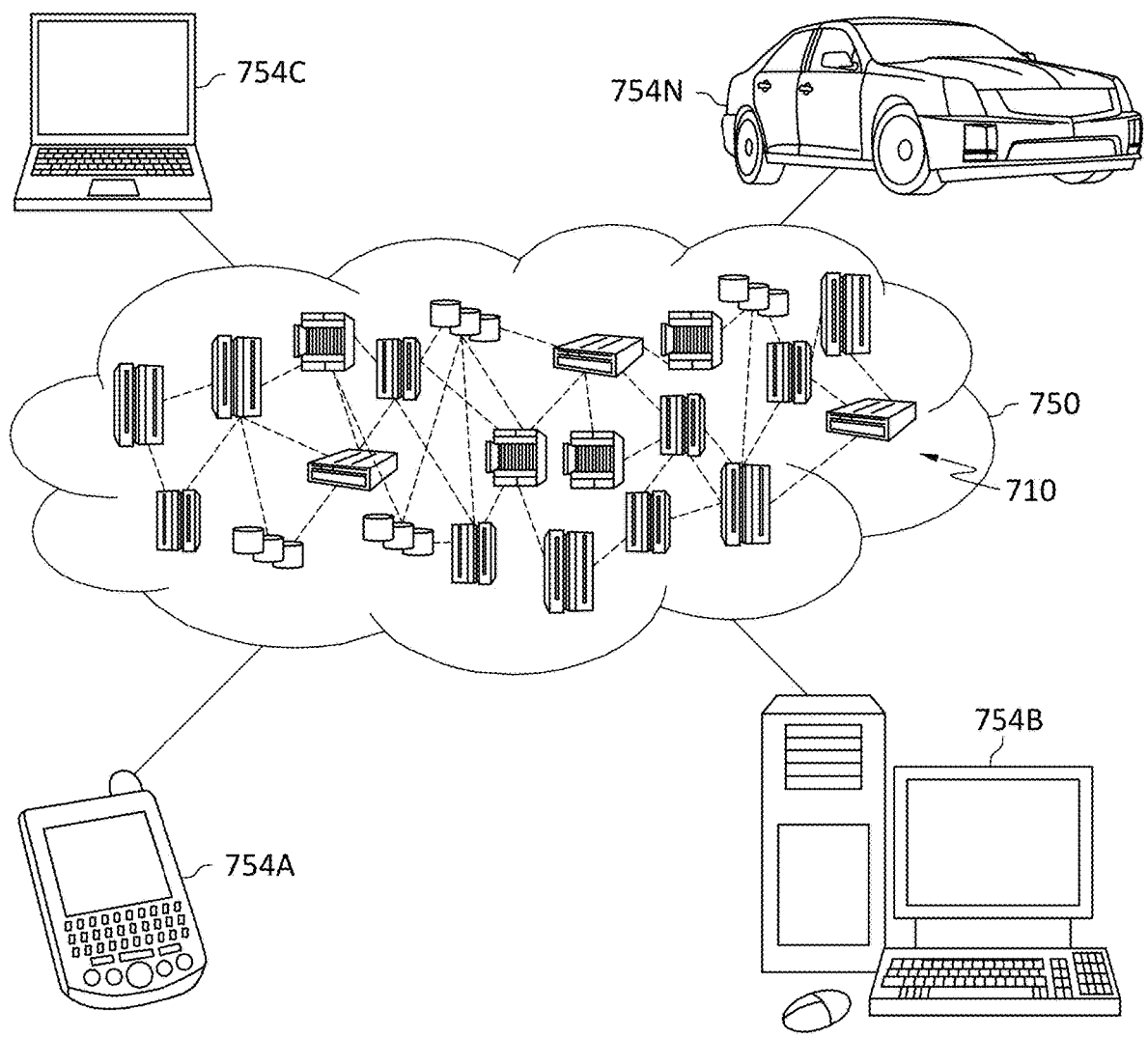
FIG. 7 is a block diagram of an illustrative cloud computing environment having one or more computing nodes with which local computing devices used by cloud customers to communicate, according to embodiments.

Referring now to FIG. 7, illustrative cloud computing environment 750 is depicted. As shown, cloud computing environment 750 includes one or more cloud computing nodes 710 with which local computing devices used by cloud consumers, such as, for example, personal digital assistant (PDA) or cellular telephone 754A, desktop computer 754B, laptop computer 754C, and/or automobile computer system 754N may communicate. Nodes 710 may communicate with one another. They may be grouped (not shown) physically or virtually, in one or more networks, such as Private, Community, Public, or Hybrid clouds as described hereinabove, or a combination thereof. This allows cloud computing environment 750 to offer infrastructure, platforms and/or software as services for which a cloud consumer does not need to maintain resources on a local computing device. It is understood that the types of computing devices 754A-N shown in FIG. 7 are intended to be illustrative only and that computing nodes 710 and cloud computing environment 750 can communicate with any type of computerized device over any type of network and/or network addressable connection (e.g., using a web browser).

Figure 8:
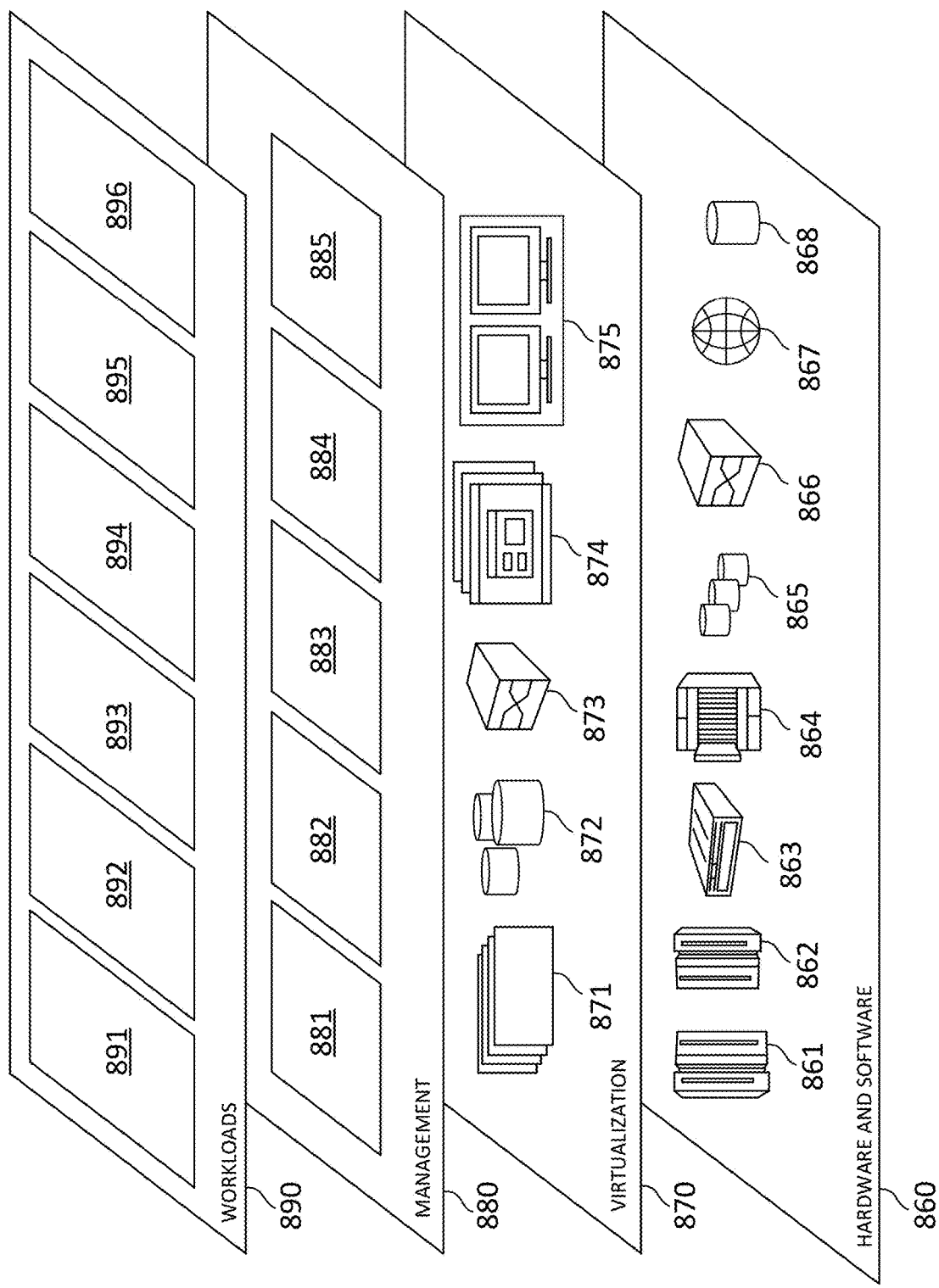
FIG. 8 is a block diagram of a set of functional abstraction layers provided by a cloud computing environment, according to embodiments.

Referring now to FIG. 8, a set of functional abstraction layers provided by cloud computing environment 750 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 860 includes hardware and software components. Examples of hardware components include: mainframes 861; RISC (Reduced Instruction Set Computer) architecture-based servers 862; servers 863; blade servers 864; storage devices 865; and networks and networking components 866. In some embodiments, software components include network application server software 867 and database software 868.

Virtualization layer 870 provides an abstraction layer from which the following examples of virtual entities may be provided: virtual servers 871; virtual storage 872; virtual networks 873, including virtual private networks; virtual applications and operating systems 874; and virtual clients 875.

In one example, management layer 880 may provide the functions described below. Resource provisioning 881 provides dynamic procurement of computing resources and other resources that are utilized to perform tasks within the cloud computing environment. Metering and Pricing 882 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 783 provides access to the cloud computing environment for consumers and system administrators. Service level management 884 provides cloud computing resource allocation and management such that required service levels are met. Service Level Agreement (SLA) planning and fulfillment 885 provide pre-arrangement for, and procurement of, cloud computing resources for which a future requirement is anticipated in accordance with an SLA.

Workloads layer 890 provides examples of functionality for which the cloud computing environment may be utilized. Examples of workloads and functions which may be provided from this layer include: mapping and navigation 891; software development and lifecycle management 892; virtual classroom education delivery 893; data analytics processing 894; transaction processing 895; and neural network CECT CP classification processing 896.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions.

The descriptions of the various embodiments have been presented for purposes of illustration and are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for classifying and presenting a contrast phase (CP) of a contrast enhanced computerized tomography (CECT) scan comprising:
    training an artificial intelligence (AI) algorithm utilizing a set of CPs labeled CECT data to associate a set of characteristics of the data with a probability associated with the CP;
    receiving a new set of unlabeled CECT data;
    applying the AI algorithm to the new unlabeled CECT data to associate a first probability of a first CP and a second probability of a second CP; and
    providing a graphical representation including the first probability of the first CP and the second probability of the second CP.

2. The computer-implemented method according to claim 1, wherein the CP is selected from the group consisting of pre-contrast, early arterial, arterial, portal-venous, nephrogenic, and late.

3. The computer-implemented method according to claim 1, wherein the graphical representation is in a form of a polygon.

4. The computer-implemented method according to claim 3, wherein a number of sides of the polygon corresponds to a number of the CPs, and each vertex of the polygon corresponds to a different one of the CPs.

5. The computer-implemented method according to claim 4, wherein locations of the vertices of the polygon correspond to 100% probabilities for the respective CP.

6. The computer-implemented method according to claim 4, wherein the graphical representation includes at least one marker located on an edge of the polygon or in an interior of the polygon, wherein distances from the marker to the respective vertices correspond to probabilities that the CP of the new unlabeled CECT data corresponds to the CP associated with the respective vertices.

7. The computer-implemented method according to claim 1, further comprising assigning an AI model to process the new unlabeled CECT data based on the first probability of the first contrast phase.

8. The computer-implemented method according to claim 1, further comprising:

determining that the first probability exceeds a threshold probability;
assigning an AI model that is associated with the first contrast phase; and
processing the new unlabeled CECT data with the AI model to determine at least one anomaly.

9. A computer system comprising:
one or more computer readable storage media with program instructions collectively stored on the one or more computer readable storage media; and
one or more processors configured to execute the program instructions to perform a method for generating a training model for object detection, the method comprising:
training an artificial intelligence (AI) algorithm utilizing a set of CPs labeled CECT data to associate a set of characteristics of the data with a probability associated with the CP;
receiving a new set of unlabeled CECT data;
applying the AI algorithm to the new unlabeled CECT data to associate a first probability of a first CP and a second probability of a second CP; and
providing a graphical representation including the first probability of the first CP and the second probability of the second CP.

10. The computer system according to claim 9, wherein the graphical representation is in a form of a polygon.

11. The computer system according to claim 10, wherein a number of sides of the polygon correspond to a number of the CPs, and each vertex of the polygon corresponds to a different one of the CPs.

12. The computer system according to claim 11, wherein locations of the vertices of the polygon corresponds to 100% probabilities for the respective CP.

13. The computer system according to claim 11, wherein the graphical representation includes at least one marker located on an edge of the polygon or in an interior of the polygon, wherein distances from the marker to the respective vertices correspond to probabilities that the CP of the new unlabeled CECT data corresponds to the CP associated with the respective vertices.

14. The computer system according to claim 9, assigning an AI model to process the new unlabeled CECT data based on the first probability of the first contrast phase.

15. The computer system according to claim 9, further comprising:
determining that the first probability exceeds a threshold probability;
assigning an AI model that is associated with the first contrast phase; and
processing the new unlabeled CECT data with the AI model to determine at least one anomaly.

16. A computer program product for context aware anomaly detection, the computer program product comprising:
one or more computer readable storage media, and program instructions collectively stored on the one or more computer readable storage media, the program instructions comprising:
program instructions to train an artificial intelligence (AI) algorithm utilizing a set of CPs labeled CECT data to associate a set of characteristics of the data with a probability associated with the CP;
program instructions to receive a new set of unlabeled CECT data;
program instruction to apply the AI algorithm to the new unlabeled CECT data to associate a first probability of a first CP and a second probability of a second CP; and
program instructions to provide a graphical representation including the first probability of the first CP and the second probability of the second CP.

17. The computer program product according to claim 16, wherein the graphical representation is in a form of a polygon.

18. The computer program product according to claim 17, wherein a number of sides of the polygon corresponds to a number of the CPs, and each vertex of the polygon corresponds to a different one of the CPs.

19. The computer program product according to claim 18, wherein locations of the vertices of the polygon correspond to 100% probabilities for the respective CP.

20. The computer program product according to claim 18, wherein the graphical representation includes at least one marker located on an edge of the polygon or in an interior of the polygon, wherein distances from the marker to the respective vertices correspond to probabilities that the CP of the new unlabeled CECT data corresponds to the CP associated with the respective vertices.

* * * * *